(12) United States Patent
Lin

(10) Patent No.: US 6,179,219 B1
(45) Date of Patent: Jan. 30, 2001

(54) VEHICLE AIR-FRESHENER

(76) Inventor: Ching-Chen Lin, No. 6, Alley 16, Lane 100, Tungshan Rd., Sec. 2, Peitun Dist., Taichung City (TW)

(*) Notice: Under 35 U.S.C. 154(b), the term of this patent shall be extended for 0 days.

(21) Appl. No.: 09/518,633

(22) Filed: Mar. 3, 2000

(51) Int. Cl.[7] .................. A61L 9/04; A24F 25/00
(52) U.S. Cl. .................. 239/44; 239/34; 222/500
(58) Field of Search .................. 239/34, 44, 51.5, 239/57, 60, 274; 222/187, 500

(56) References Cited

U.S. PATENT DOCUMENTS

| | | | |
|---|---|---|---|
| 3,031,146 | * 4/1962 | Albamonte | 239/60 X |
| 3,111,244 | * 11/1963 | Mills | 222/500 X |
| 4,619,383 | * 10/1986 | Konicek | 222/556 |
| 4,660,764 | * 4/1987 | Joyaux et al. | 239/44 |
| 6,015,094 | * 1/2000 | Por | 239/44 |

* cited by examiner

*Primary Examiner*—Andres Kashnikow
*Assistant Examiner*—Robin O. Evans
(74) *Attorney, Agent, or Firm*—Rosenberg, Klein & Lee

(57) ABSTRACT

A vehicle air-freshener includes a holder base for mounting inside a motor vehicle, a container body mounted on the holder base and holding a perfume, the container body having a recessed top side wall, and a top center through hole formed through the lowest area of the recessed top side wall for enabling the smell of the perfume to escape out of the container body into the air, a control ball moved in the recessed top side wall of the container body to close/open the top center through hole, and a perforated cap covered on the container body to hold the control ball in the recessed top side wall of the container body.

5 Claims, 3 Drawing Sheets

VEHICLE AIR-FRESHENER

BACKGROUND OF THE INVENTION

The present invention relates to a vehicle air-freshener, and more particularly to such a vehicle air-freshener, which uses a rolling ball to automatically close the perfume dispensing output hole when the motor vehicle stops, or to open the perfume dispensing output hole when the motor vehicle moves.

Regular vehicle air-fresheners commonly comprise a container body holding a perfume, and a cap controlled to open/close the container body. When not in use, the cap is closed with the hand to prevent escaping of the good smell of the perfume. When in use, the cap is opened with the hand to let the good smell of the perfume escape out of the container body into the inside of the motor vehicle. Because of manual control, it is complicated to open/close the container body. If the user forgets to close the container body when leaving the motor vehicle, the smell of the perfume continuously escapes out of the container body into the closed space in the motor vehicle. When a thick smell is accumulated in the motor vehicle, it will irritate the nose. During the hot season, the perfume will be used up quickly.

SUMMARY OF THE INVENTION

The present invention has been accomplished to provide a vehicle air-freshener, which eliminates the aforesaid problems. It is the main object of the present invention to provide a vehicle air-freshener, which automatically controls the dissipation of the good smell of a perfume. According to one aspect of the present invention, the vehicle air-freshener comprises a holder base, a container body holding a perfume, the container body having a top through hole on a recessed top side wall thereof, a perforated cap covered on the container body, and a control ball moved in the recessed top side wall of the container body within the perforated cap. When the motor vehicle is stopped, the control ball falls to the top through hole to close the perfume dispensing passage. When the motor vehicle is moving, the control ball is moved with the body of the motor vehicle to open the top through hole, enabling the good smell of the perfume to escape out of the container body and the perforated cap into the air inside the motor vehicle. According to another aspect of the present invention, the position of the container body can be adjusted relative to the holder base. If the holder base is not installed in a horizontal surface inside the motor vehicle, the position of the container body can be adjusted to horizontal.

DETAILED DESCRIPTION OF THE PREFERRED EMBODIMENT

Figures 1, 1A, 1B:
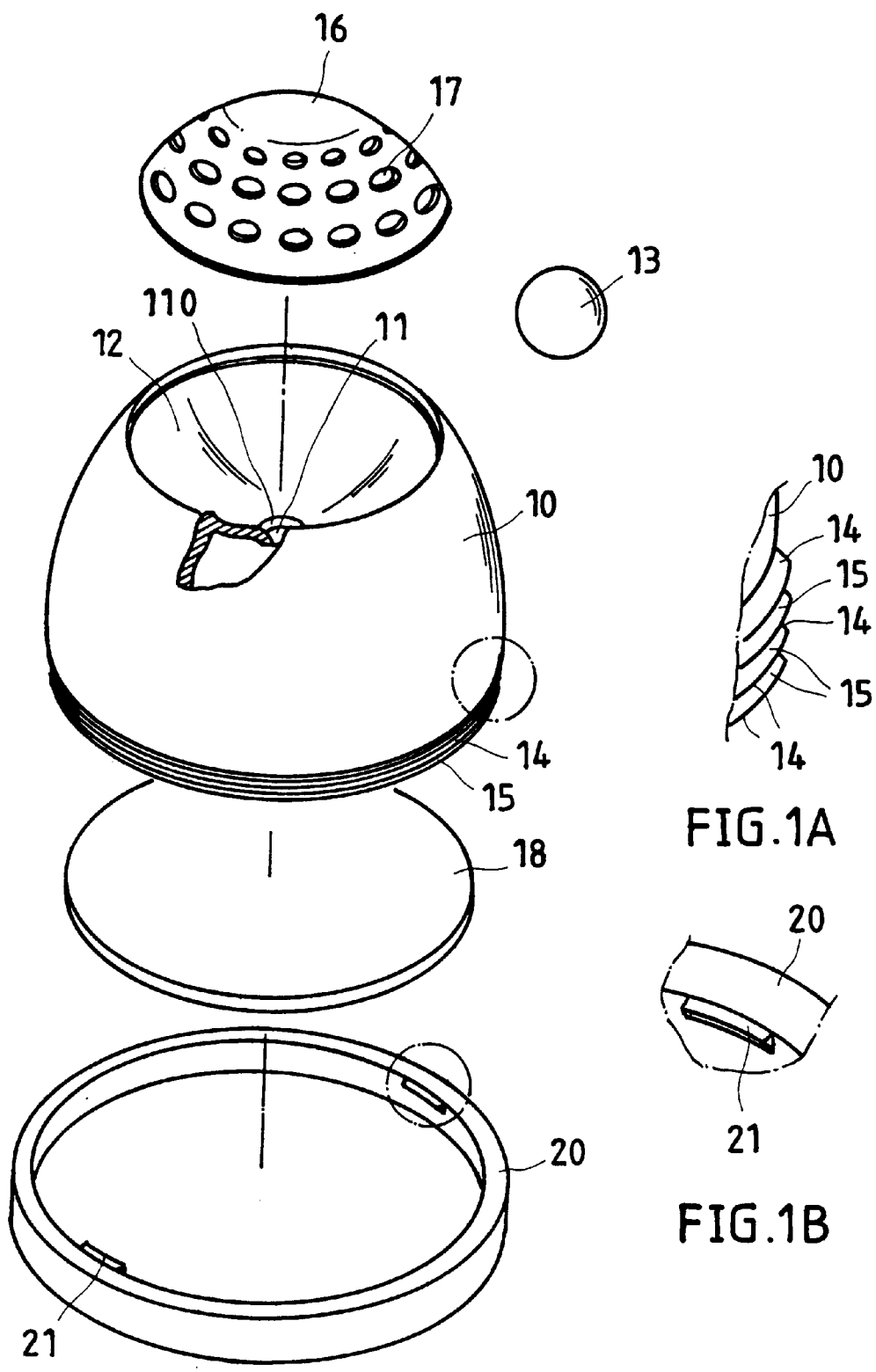
FIG. 1 is an exploded view of a vehicle air-freshener according to the present invention.
FIG. 1A is an enlarged view of a part of the container body of the vehicle air-freshener shown in FIG. 1.
FIG. 1B is an enlarged view of a part of the holder base of the vehicle air-freshener shown in FIG. 1.
Figure 2:
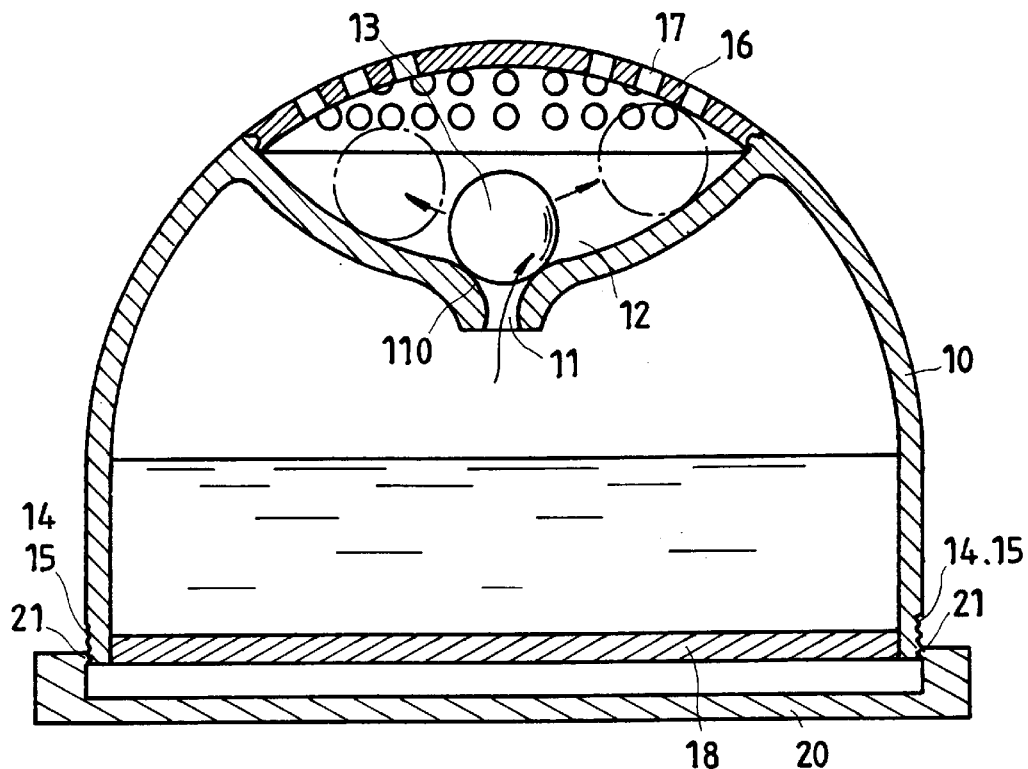
FIG. 2 is a sectional assembly view of the present invention.

Referring to FIGS. 1, 1A, 1B and 2, a vehicle air-freshener in accordance with the present invention is shown comprised of an air-freshener container body 10 having a bottom cover 18, a control ball 13 mounted in the container body 10, a cap 16 covered on the container body 10, and a holder base 20 holding the container body 10. The cap 16 has air vents 17 for dissipation of good smell from the liquid perfume in the container body 10 into the outside air. The container body 10 is a hollow shell having a recessed top side wall 12, a top center through hole 11 at the center of the recessed top side wall 12, and a plurality of positioning flanges 14 and positioning grooves 15 alternatively arranged at different elevations around the periphery near the bottom side thereof. The recessed top sidewall 12 curves inwards toward the top center through hole 11. The top center through hole 11 has a tapered top orifice 110. The control ball 13 is moved within the recessed top sidewall 12 to close/open the top center through hole 11. The holder base 20 is a flat, cup-like holder member fastened to the inside of a motor vehicle, having two locating flanges 21 bilaterally disposed on the inside for engaging into the positioning grooves 15 on the container body 10 to hold the container body 10 on the holder base 20.

Referring to FIG. 2 again, when the motor vehicle is not moving, the control ball 13 falls to the lowest position in the recessed top sidewall 12 to close the passage of the top center through hole 11, and therefore the liquid perfume is sealed in the container body 10. When the motor vehicle moves, the air-freshener is moved with the body of the motor vehicle, causing the control ball 13 to be moved in the recessed top sidewall 12. During motion of the control ball 13, the top center through hole 11 is opened, and the good smell of the liquid perfume escapes out of the container body 10 through the top center through hole 11 into the air inside the motor vehicle via the air vents 17 in the cap 16. Because the recessed top sidewall 12 curved inwards toward the top center through hole 11 and because the top center through hole 11 has a tapered top orifice 110, the control ball 13 automatically quickly falls to the top orifice 110 to close the top center through hole 11 when the motor vehicle is immovable. This design automatically controls the dispensing of the liquid perfume subject to the status of the motor vehicle. When the motor vehicle moves, the good smell of the liquid perfume is automatically dispensed. On the contrary, when the motor vehicle stops, the dispensing of the good smell of the liquid perfume is automatically stopped. This automatic dispensing design prevents quick changing of the liquid perfume into vapor.

Figure 3:
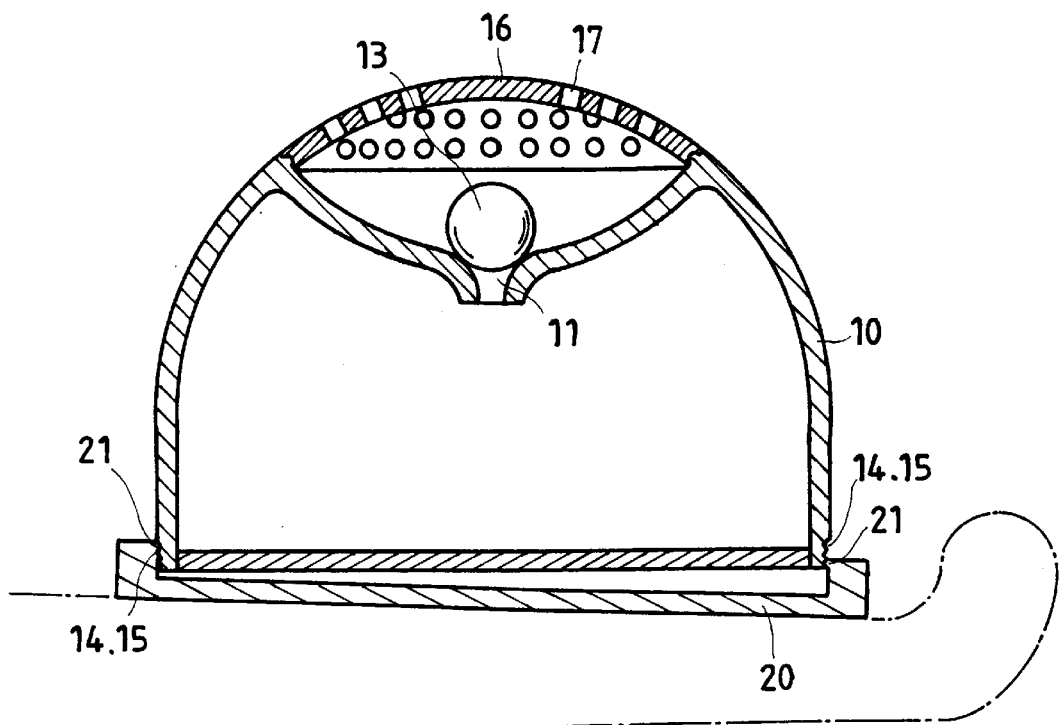
FIG. 3 is a sectional view showing the position of the container body adjusted.

Referring to FIG. 3, if the holder base 20 is not installed in a horizontal position inside the motor vehicle, the engagement between the positioning grooves 15 on the container body 10 and the locating flanges 21 of the holder base 20 can be adjusted to keep the container body 10 in horizontal.

Figure 4:
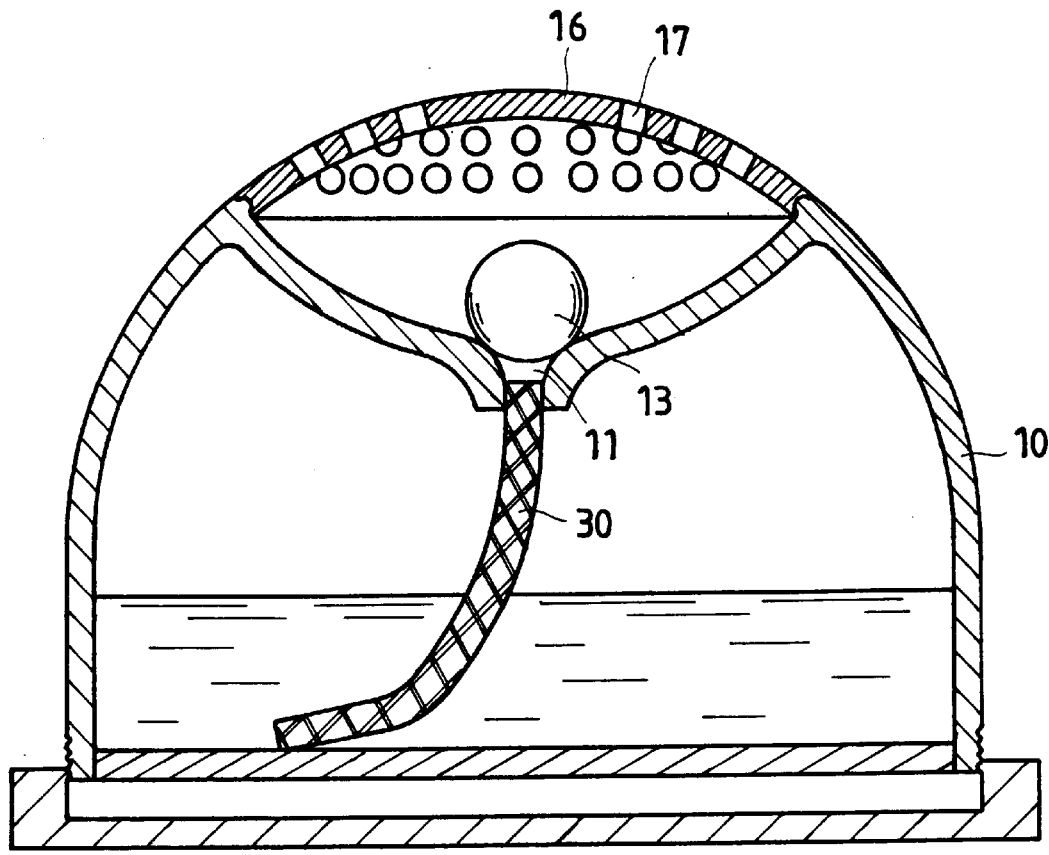
FIG. 4 is similar to FIG. 2 but showing an absorptive core member installed in the container body.

Referring to FIG. 4, an absorptive core member 30 may be fastened to the top center through hole 11 in the container body 10 and dipped in the liquid perfume, enabling the good smell of the liquid perfume to be smoothly dissipating into the air after opening of the control ball 13 from the top center through hole 11.

Figure 5:
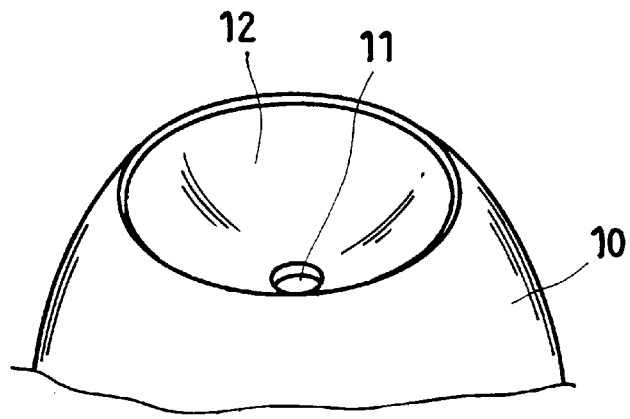
FIG. 5 illustrates an alternate form of the container body for the vehicle air-freshener according to the present invention.

Further, the recessed top sidewall 12 of the container body 10 may be variously shaped. In the embodiment shown in FIGS. from 1 through 4, the recessed top sidewall 12 defines a rounded recess. FIG. 5 shows an alternate form of recessed top sidewall 12 of the container body 10. The container body 10 can also be variously shaped. For example, the container body 10 can have a rectangular shape, a square shape, a conical shape, etc.

It is to be understood that the drawings are designed for purposes of illustration only, and are not intended for use as a definition of the limits and scope of the invention disclosed. For example, the body 10 can be made having a detachable bottom cover 18 for holding a solid perfume.

What the invention claimed is:

1. A vehicle air-freshener comprising:

a holder base for mounting inside a motor vehicle;

a container body mounted on said holder base and holding a perfume, said container body comprising a recessed top side wall, and a top center through hole formed through the lowest area of said recessed top side wall for enabling the smell of said perfume to escape out of said container body into the air;

a control ball moved in the recessed top sidewall of said container body to close/open said top center through hole;

a cap covered on said container body to hold said control ball in said recessed top sidewall, said cap having a plurality of air vents.

2. The vehicle air-freshener of claim 1 wherein said container body comprises a plurality of positioning grooves disposed around the periphery thereof at different elevations for positioning in said holder base, and said holder base comprises a plurality of locating flanges symmetrically disposed on the inside for engaging into the positioning grooves to hold said container body in said holder base.

3. The vehicle air-freshener of claim 1 wherein said top center through hole of said container body has a tapered top orifice.

4. The vehicle air-freshener of claim 1 wherein said perfume is a liquid perfume, and said container body comprises an absorptive core member having a top end fastened to said top center through hole and a bottom end dipped in said liquid perfume.

5. The vehicle air-freshener of claim 1 wherein said perfume is a solid perfume.

* * * * *